(12) United States Patent
Wilson et al.

(10) Patent No.: US 9,945,815 B2
(45) Date of Patent: Apr. 17, 2018

(54) METHODS AND SYSTEMS FOR DETECTING DEFECTS IN A FUEL CELL STACK

(71) Applicant: BLOOM ENERGY CORPORATION, Sunnyvale, CA (US)

(72) Inventors: James Wilson, San Francisco, CA (US); Arne Ballantine, Palo Alto, CA (US); Matthias Gottmann, Sunnyvale, CA (US); Tad Armstrong, Burlingame, CA (US); Martin Perry, Mountain View, CA (US); David Edmonston, Santa Cruz, CA (US); Michael Lesher, Sunnyvale, CA (US); Joshua Baime, Mountain View, CA (US)

(73) Assignee: BLOOM ENERGY CORPORATION, Sunnyvale, CA (US)

(*) Notice: Subject to any disclaimer, the term of this patent is extended or adjusted under 35 U.S.C. 154(b) by 128 days.

(21) Appl. No.: 14/792,923

(22) Filed: Jul. 7, 2015

(65) Prior Publication Data

US 2016/0011071 A1  Jan. 14, 2016

Related U.S. Application Data

(60) Provisional application No. 62/022,942, filed on Jul. 10, 2014.

(51) Int. Cl.
*G01M 3/04* (2006.01)
*G01N 29/04* (2006.01)
(Continued)

(52) U.S. Cl.
CPC ............ *G01N 29/04* (2013.01); *G01M 3/226* (2013.01); *G01N 33/0054* (2013.01)

(58) Field of Classification Search
CPC ..... H01M 2008/1095; H01M 2250/20; H01M 2008/1293; H01M 8/04753; Y02P 70/56
(Continued)

(56) References Cited

U.S. PATENT DOCUMENTS 2,176,784 A   10/1939   Bowden
5,589,772 A   12/1996   Kugai
(Continued)

FOREIGN PATENT DOCUMENTS

JP   2000-285934 A   10/2000
JP   2007-042406 A    2/2007
KR   10-2010-0109253 A   10/2010

OTHER PUBLICATIONS

International Search Report & Written Opinion, PCT/US2011/062328, dated Aug. 1, 2012.
(Continued)

*Primary Examiner* — Eric S McCall
*Assistant Examiner* — Mohammed E Keramet-Amircolai
(74) *Attorney, Agent, or Firm* — The Marbury Law Group PLLC

(57) ABSTRACT

A method for testing a fuel cell stack includes providing a fluid, such as an ammonia-containing fluid, in a first reactant flow path in a first portion of the fuel cell stack, detecting the presence of the fluid using a detector, such as an ammonia detector, positioned within or adjacent to a second portion of the fuel cell stack that is separated from the first portion of the fuel cell stack and determining the presence of a defect in the stack based on detecting the presence of the fluid. Further embodiments relate to testing a fuel cell stack using a microphone that detects an audio signal indicative of a stack defect.

20 Claims, 7 Drawing Sheets

(51) Int. Cl.
*G01N 33/00* (2006.01)
*G01M 3/22* (2006.01)

(58) Field of Classification Search
USPC .................................. 73/40.7, 45, 61.61
See application file for complete search history.

(56) References Cited

U.S. PATENT DOCUMENTS

| | | | |
|---|---|---|---|
| 6,426,161 B1 | 7/2002 | Cisar et al. | |
| 6,599,651 B1* | 7/2003 | Saitou | H01M 8/0206 429/492 |
| 8,802,331 B2* | 8/2014 | Herchen | G01N 21/95 324/200 |
| 2004/0095127 A1 | 5/2004 | Mohri et al. | |
| 2005/0142431 A1 | 6/2005 | Shimomura et al. | |
| 2006/0127711 A1 | 6/2006 | Kaschmitter et al. | |
| 2006/0228613 A1* | 10/2006 | Bourgeois | H01M 8/0282 429/432 |
| 2008/0199738 A1 | 8/2008 | Perry et al. | |
| 2010/0021778 A1* | 1/2010 | Steinshnider | B01D 19/0042 429/419 |
| 2010/0225339 A1* | 9/2010 | Fujita | G01N 27/4067 324/699 |
| 2012/0135337 A1 | 5/2012 | Herchen et al. | |
| 2012/0189940 A1* | 7/2012 | Richards | H01M 8/06 429/471 |
| 2013/0230072 A1 | 9/2013 | Couse et al. | |
| 2013/0269436 A1* | 10/2013 | Couse | G01N 29/12 73/582 |

OTHER PUBLICATIONS

Huth et al., "Lock-in IR-Thermography—a novel tool for material and device characterization," Solid State Phenomena 82-84, pp. 741-746 (2002).
Low Cost, High Efficiency Reversible Fuel Cell (and Electrolyzer) Systems, Proceedings of the 2001 DOE Hydrogen Program Review NREL/CP-570-30535.
International Search Report and Written Opinion received in connection with international application No. PCT/US2013/035895, dated Jul. 25, 2013.
International Preliminary Report on patentability received in connection with international application No. PCT/US2013/035895, dated Oct. 23, 2014.
Fialkov, A. S. et al., "Diamagnetic Susceptibility and Linear Thermal Expansion of Graphitized Carbons," Translated from Poroshkovaya Metallurgiya, vol. 32, No. 8, pp. 87-95, (1965).

* cited by examiner

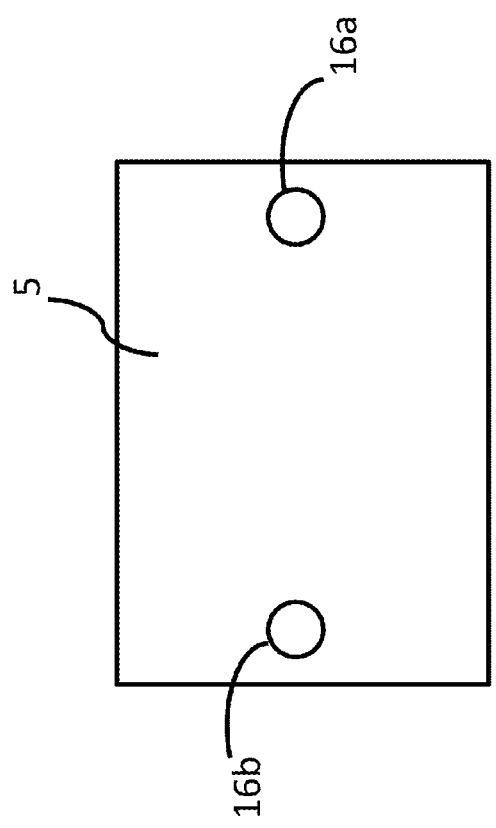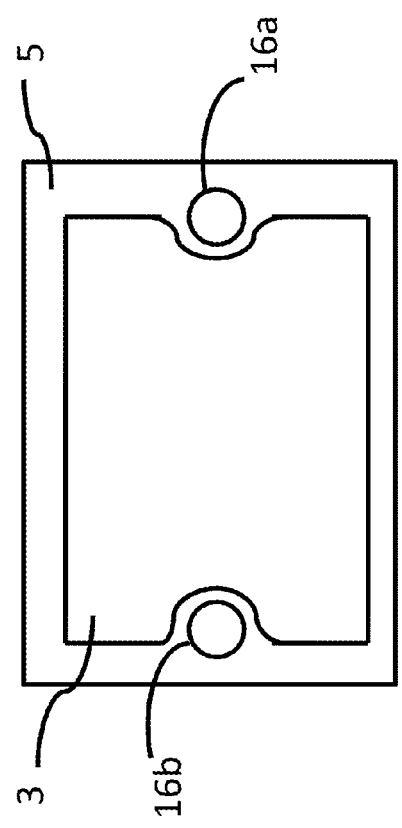

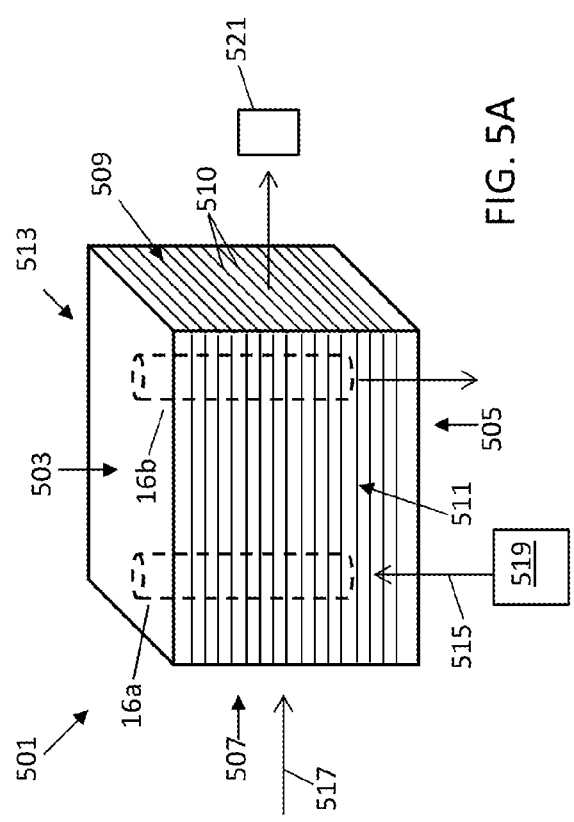
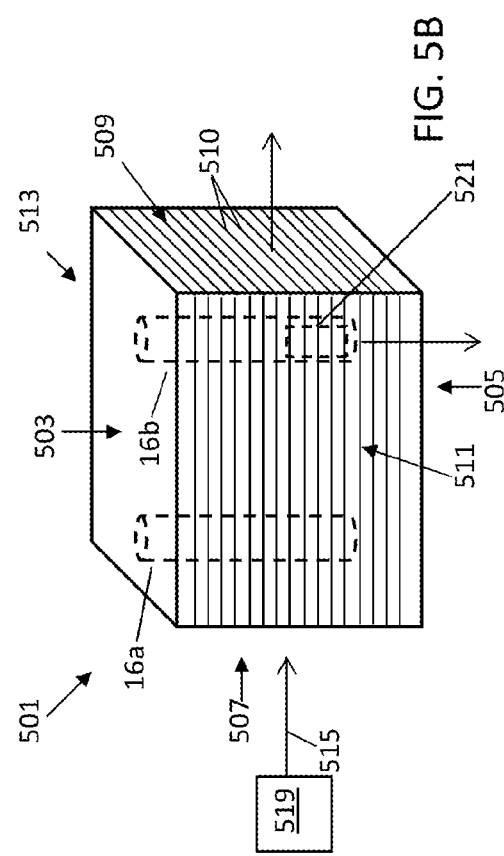

METHODS AND SYSTEMS FOR DETECTING DEFECTS IN A FUEL CELL STACK

RELATED APPLICATION

This application claims the benefit of priority to U.S. Provisional Application No. 62/022,942, filed on Jul. 10, 2014, the entire contents of which are incorporated by reference herein.

BACKGROUND

In a high temperature fuel cell system, such as a solid oxide fuel cell (SOFC) system, an oxidizing flow is passed through the cathode side of the fuel cell while a fuel flow is passed through the anode side of the fuel cell. The oxidizing flow is typically air, while the fuel flow can be a hydrocarbon fuel, such as methane, natural gas, pentane, ethanol, or methanol. The fuel cell, operating at a typical temperature between 750° C. and 950° C., enables the transport of negatively charged oxygen ions from the cathode flow stream to the anode flow stream, where the ion combines with either free hydrogen or hydrogen in a hydrocarbon molecule to form water vapor and/or with carbon monoxide to form carbon dioxide. The excess electrons from the negatively charged ion are routed back to the cathode side of the fuel cell through an electrical circuit completed between anode and cathode, resulting in an electrical current flow through the circuit. A plurality of fuel cells may be assembled in a fuel cell stack, with electrically conductive interconnects located between each fuel cell of the stack.

SUMMARY

Various embodiments include methods for testing a fuel cell stack that include providing a fluid, such as an ammonia-containing fluid, in a first reactant flow path in a first portion of the fuel cell stack, detecting the presence of the fluid using a detector, such as an ammonia detector, positioned within or adjacent to a second portion of the fuel cell stack that is separated from the first portion of the fuel cell stack and determining the presence of a defect in the stack based on detecting the presence of the fluid.

Further embodiments include methods for testing a fuel cell stack that include providing a pressurized fluid in a first reactant flow path of the fuel cell stack, detecting an audio signal using a microphone positioned within or adjacent to a second portion of the stack that is separated from the first reactant flow path, and determining the presence of a defect in the stack based on the detected audio signal.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIG. 4A is a plan view of an electrolyte of a fuel cell.

FIG. 4B is a plan view of an electrolyte and an anode electrode of a fuel cell.

FIG. 5A schematically illustrates a perspective view of a fuel cell stack testing method using an ammonia detector according to an embodiment.

FIG. 5B schematically illustrates a perspective view of fuel cell stack testing method using an ammonia detector according to another embodiment.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

In one aspect, the present invention provides accurate, rapid and non-destructive techniques for detecting defects in a fuel cell stack. Various embodiments include methods of testing an assembled fuel cell stack which may enable particular stack defects, such as defective seal(s) and/or cracks in an electrolyte, to be identified and located. Thus, the use of defective fuel cell stacks in a fuel cell system may be avoided. In some embodiments, defective components of the fuel cell stack identified with the embodiment method may be removed and replaced prior to utilizing the stack in a fuel cell system. In various embodiments, the testing method may be performed at a temperature that is significantly lower than the operating temperature of the fuel cell stack, and may be performed at a temperature between 0° C. and 50° C., such as between 20° C. and 30° C. (e.g., at room temperature).

Figure 1:
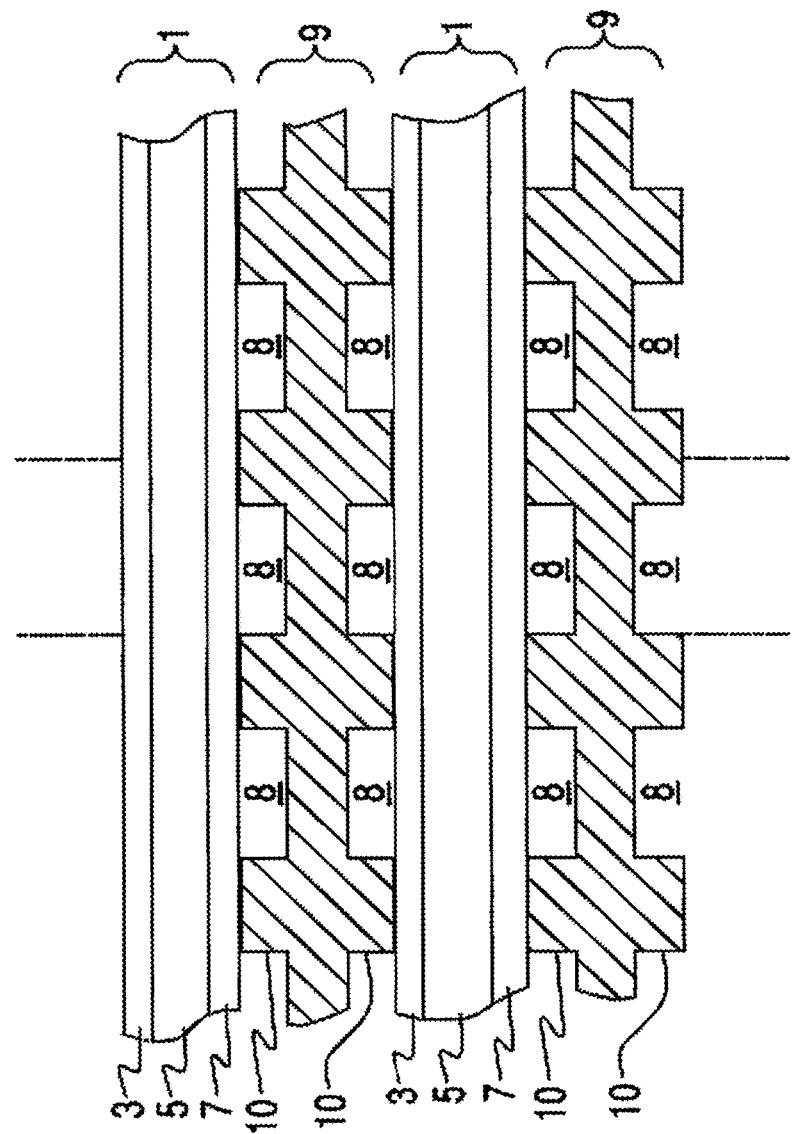
FIG. 1 illustrates a side cross-sectional view of a SOFC stack.

An example of a solid oxide fuel cell (SOFC) stack is illustrated in FIG. 1. Each SOFC 1 comprises a cathode electrode 7, a solid oxide electrolyte 5, and an anode electrode 3. The solid oxide fuel cell illustrated in this figure is an electrolyte supported cell in which the ceramic electrolyte 5 material can be a stabilized zirconia, such as scandia stabilized zirconia (SSZ) or yttria stabilized zirconia (YSZ). Alternatively, the electrolyte may comprise another ionically conductive material, such as a doped ceria. The cathode electrode 7 may comprise a thin layer of electrically conductive perovskite material, such as lanthanum strontium manganate (LSM), while the anode electrode 3 may comprise a thin layer of cermet material containing metal and ceramic phases, such as a nickel metal phase and a stabilized zirconia (e.g., SSZ or YSZ) or doped ceria ceramic phase (e.g., samaria doped ceria, SDC).

Fuel cell stacks are frequently built from a multiplicity of SOFC's 1 in the form of planar elements, tubes, or other geometries. Fuel and air has to be provided to the electrochemically active surface, which can be large.

The gas flow separator 9 (referred to as a gas flow separator plate when part of a planar stack), containing gas flow passages or channels 8 between ribs 10, separates the individual cells in the stack. The ribs 10 on opposite sides of the plate may be offset from each other, as described in U.S. Published Patent Application Number 2008/0199738 A1 (filed on Feb. 16, 2007 as U.S. application Ser. No. 11/707, 070) which is incorporated herein by reference in its entirety. Frequently, the gas flow separator plate 9 is also used as an interconnect which electrically connects the anode or fuel electrode 3 of one cell to the cathode or air electrode 7 of the adjacent cell. In this case, the gas flow separator plate which functions as an interconnect is made of or contains electrically conductive material. The interconnect/gas flow separator 9 separates fuel, such as a hydrocarbon fuel, flowing to the fuel electrode (i.e. anode 3) of one cell in the stack from oxidant, such as air, flowing to the air electrode (i.e. cathode 7) of an adjacent cell in the stack. FIG. 1 shows that the lower SOFC 1 is located between two interconnects 9.

Figure 2:
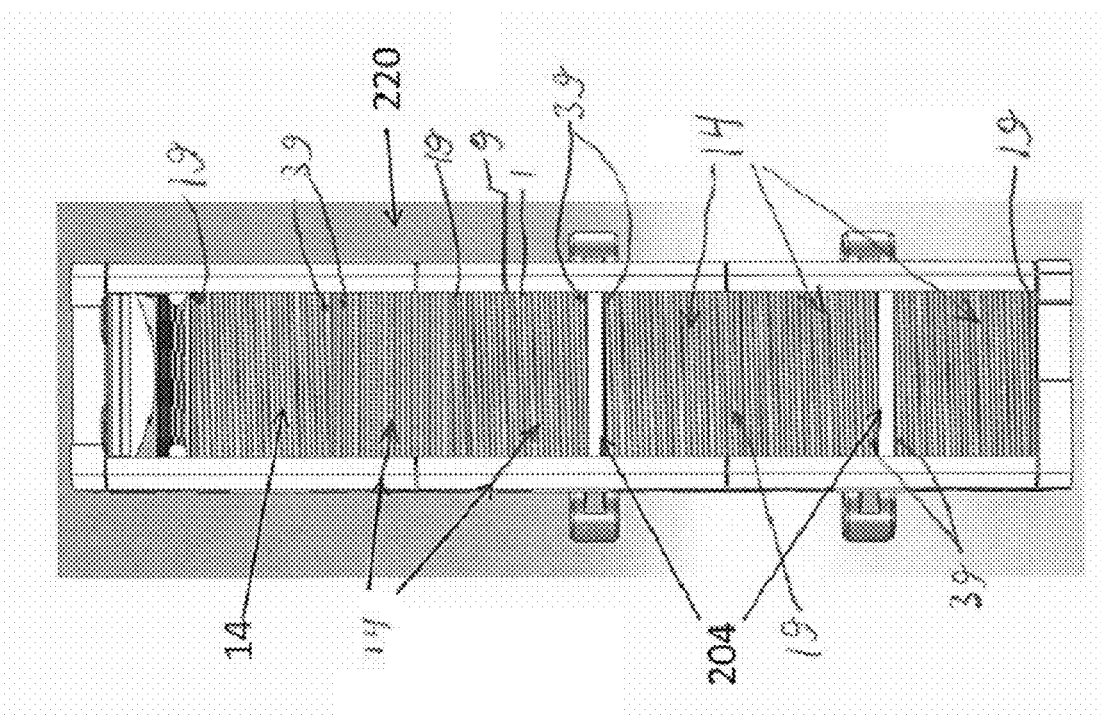
FIG. 2 illustrates a side view of an embodiment of a column of fuel cell stacks with plate shaped side baffles.

FIG. 2 illustrates a column containing one or more fuel cell stacks 14. Each fuel cell stack contains a plurality of the SOFCs 1 and interconnects 9, one air end plate 19 and one fuel end plate 39. As shown in FIG. 2, at either end of the stack 14, there may be an air end plate 19 or fuel end plate 39 for providing air or fuel, respectively, to the end electrode. The air end plate 19 faces the final cathode electrode 7 of the stack at one end of the stack (e.g., top or bottom end of the stack), while the fuel end plate 39 faces the final anode electrode 3 of the stack at the opposite end of the stack (e.g., bottom or top end of the stack).

Optionally, two side baffles 220 are placed on opposite sides of the stack. However, more or less side baffles 220 may be used for stacks having a cross sectional shape other than rectangular. Further, one or more fuel manifolds 204 may be provided in the column of fuel cell stacks 14. An exemplary fuel manifold is described in the U.S. application Ser. No. 11/656,563 incorporated by reference herein in its entirety. Any number of fuel manifolds 204 may be provided between adjacent fuel cell stacks 14 as desired. Further, the number of fuel cell stacks 14 in a column of fuel cell stacks 14 may be selected as desired and is not limited to the number of fuel cell stacks 14 illustrated in FIG. 2.

Figure 3A:
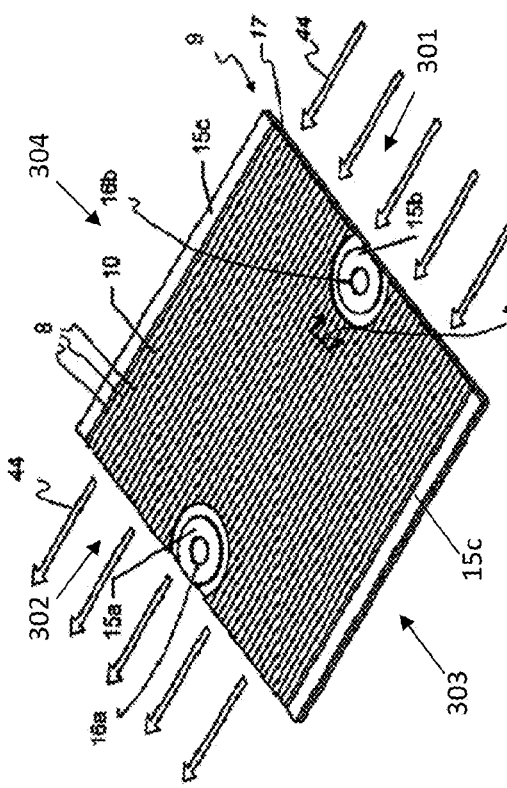
FIG. 3A is a perspective view of a cathode side of an interconnect.
Figure 3B:
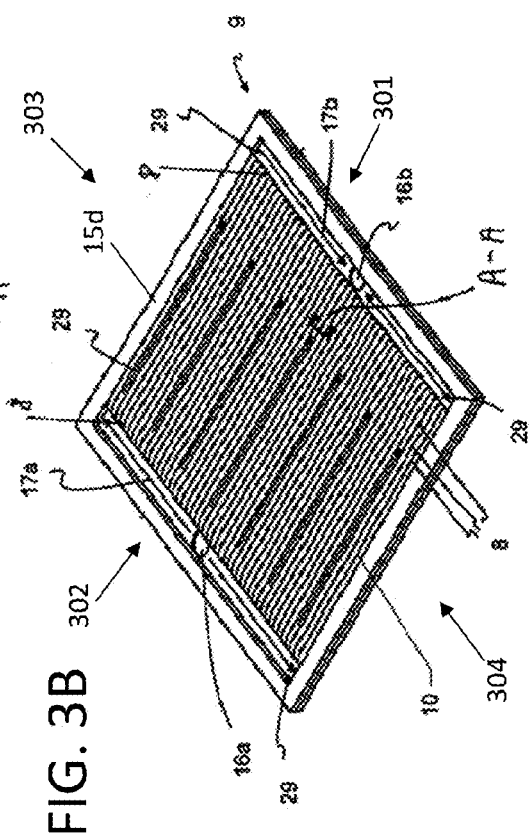
FIG. 3B is a perspective view of an anode side of an interconnect.

FIGS. 3A and 3B show, respectively, top and bottom views of an interconnect 9. The portions of interconnect 9 shown in side cross-section in FIG. 1 are provided along lines A-A in FIGS. 3A and 3B. The interconnect 9 contains gas flow passages or channels 8 between ribs 10. The interconnect 9 in this embodiment includes at least one riser channel 16a for providing fuel to the anode-side of the SOFC 1, as illustrated by arrow 29. The riser channel 16a generally comprises a fuel inlet riser opening or hole that extends through at least one layer of the fuel cells and interconnects in the stack. As illustrated in FIG. 3B, the fuel can flow through the inlet riser channel 16a to the anode-side of each fuel cell. There, the fuel can collect in an inlet plenum 17a (e.g., a groove in the interconnect's surface), then flow over the fuel cell anode 3 through gas flow channels 8 formed in the interconnect 9 to an outlet plenum 17b and then exit through a separate outlet riser channel 16b.

The cathode side, illustrated in FIG. 3A, can include gas flow passages or channels 8 between ribs 10 which direct air flow 44 over the cathode electrode of the fuel cell. The cathode side of the interconnect may include elevated portions surrounding the respective riser channels 16a, 16b and seals 15a, 15b may be provided on the elevated portions surrounding the riser channels 16a, 16b and may seal the respective riser channels 16a, 16b to the flat surface of the adjacent SOFC 1 in the stack to prevent fuel from reaching the cathode electrode of the fuel cell. The seals 15a, 15b may have a donut or hollow cylinder shape as shown so that the riser channels 16a, 16b extend through the hollow middle part of the respective seals 15a, 15b.

In the embodiment of FIG. 3A, the air flow 44 enters the gas flow passages or channels 8 on a first side 301 of the interconnect 9, flows over the cathode electrode of the fuel cell, and exits the gas flow passages or channels 8 on a second side 302 of the interconnect opposite the first side 301. The cathode side of the interconnect 9 may have elevated portions along the periphery of the third 303 and fourth 304 sides of the interconnect, and strip seals 15c may be provided on the elevated portions to seal the cathode side of the interconnect to the surface of the adjacent SOFC 1. On the anode side of the interconnect, as shown in FIG. 3B, a flat elevated surface may completely surround the periphery of the fuel flow passages 8 and a peripheral seal 15d (i.e., a window seal) may be located on the surface to seal the anode-side of the interconnect to the adjacent SOFC 1 and prevent air from reaching the anode electrode of the fuel cell.

The side of the air end plate 19 which faces the adjacent final cathode electrode 7 of the stack may have the same flow channel 8 and rib 10 geometry as the air sides of the interconnects 9 shown in FIG. 3A. However, the opposite side of the air end plate 19 which faces away from its stack does not need to have any flow channels 8 or ribs 10, since this side is used for electrical interconnection with an adjacent stack or with an electrical terminal.

The side of the fuel end plate 39 which faces the adjacent final anode electrode 3 of the stack may have the same flow channel 8 and rib 10 geometry as the fuel sides of the interconnects 9 shown in FIG. 3B. However, the opposite side of the fuel end plate 39 which faces away from its stack does not need to have any flow channels 8 or ribs 10, since this side is used for electrical interconnection with an adjacent stack or with an electrical terminal.

In FIGS. 3A and 3B, the riser channel openings 16a, 16b are shown as fuel inlet and fuel outlet openings in the interconnect 9. This interconnect is configured for a fuel cell stack which is internally manifolded for fuel, in which the fuel travels through the stack through fuel riser channels which are formed by mated openings through the stacked interconnects and fuel cells. However, if desired, the interconnect 9 may be configured for a stack which is externally manifolded for fuel. In this case, the top and bottom edges of the interconnect 9 shown in FIG. 3B would function as fuel inlet and outlet, respectively, for the fuel which flows externally to the stack. Furthermore, the interconnect 9 shown in FIGS. 3A and 3B is configured for a stack which is externally manifolded for air. However, additional openings through the interconnect may be formed, such as on the left and right sides of the interconnect, for the interconnect to be configured for a stack which is internally manifolded for air.

FIG. 4A is a plan view of a solid oxide electrolyte 5. The electrolyte 5 may comprise a stabilized zirconia, such as scandia stabilized zirconia (SSZ) or yttria stabilized zirconia (YSZ). Alternatively, the electrolyte 5 may comprise another ionically conductive material, such as a doped ceria. In this embodiment, the electrolyte 5 has a planar geometry, although it will be understood that other geometries, such as a tubular geometry, could be utilized. Riser channel openings 16a, 16b, which in this embodiment comprise circular holes, extend through the electrolyte 5. The riser channels 16a, 16b generally comprise fuel inlet and outlet openings that extend through at least one layer of the fuel cells. When the fuel cells and interconnects are assembled into a stack, such as shown in FIG. 2, the respective riser channels 16a, 16b of the fuel cells 5 and the interconnects 9 may form a continuous fluid passageway extending through multiple electrolyte layers 5 and interconnects 9. Fuel can flow in a fuel reactant path through the inlet riser channel 16a to the anode-side of each fuel cell. There, the fuel flows over the fuel cell anode 3 via gas flow channels 8 formed in the gas flow separator/interconnect plate 9, and then exits through separate outlet riser channel 16b. Air can flow in an air reactant path through inlet openings on a periphery of the stack (i.e., through the open sides 301 of the interconnects 9, as shown in FIG. 3A), over the fuel cell cathode 7 via gas flow channels 8 formed in the interconnect 9, and exit through outlet openings on a periphery of the stack (i.e., through the open sides 302 of the interconnects 9, as shown in FIG. 3B).

In FIG. 4B, an anode (e.g., fuel) electrode 3 is shown covering part of a first major surface of the electrolyte 5. A cathode (e.g., air) electrode 7 (not shown) can cover part of the second major surface on the opposite side of the electrolyte 5.

The SOFC 1 in this embodiment is configured for a stack that is internally manifolded for fuel and externally manifolded for air. Thus, the stack is open on the air inlet and outlet sides. Alternatively, the SOFC 1 may be configured for a stack which is internally manifolded for both air and fuel. In this case, the electrolyte would contain additional air inlet and outlet openings. Alternatively, the SOFC 1 may be externally manifolded for air and fuel.

In high temperature fuel cell systems, such as SOFC systems, it is difficult to identify certain types of defects, such as small cracks in the electrolyte and defective seals (e.g., seals with cracks or voids between the seal and an adjacent stack component, such as an adjacent fuel cell or interconnect). Such defects may allow mixing of the reactant streams (e.g., air and fuel) in the fuel cell stack and/or leakage of the fuel stream out of an internally-manifolded stack and may result in a shortened useful lifetime of the fuel cell stack. Typically, such defects are not identified until after the stacks are heated to their operating temperatures (e.g., 750° C. and 950° C.) and brought into an operational condition.

Various embodiments include methods for accurate, rapid and non-destructive testing of fuel cell stacks that can be performed at temperatures that are significantly lower than the stack operating temperature, including at ambient temperature. In a first embodiment, a method of testing a fuel cell stack includes providing a fluid comprising ammonia in a first reactant flow path in a first portion of the fuel cell stack, detecting the presence of ammonia using an ammonia detector positioned within or adjacent to a second portion of the fuel cell stack that is separated from the first portion of the fuel cell stack, and determining the presence of a defect in the stack based on detecting the presence of ammonia.

FIG. 5A illustrates a fuel cell stack 501 which may be a SOFC stack comprising a plurality of solid oxide fuel cells separated by conductive interconnects, as described above. The stack 501 may have a top side 503, a bottom side 505, and a plurality of side surfaces 507, 509, 511 and 513. In this embodiment, side surface 507 may be an open side surface, meaning that the side surface contains a plurality of inlet openings (not visible in FIG. 5A) located between the fuel cells and an adjacent interconnect of the stack. Side surface 509 may also be an open side surface that contains a plurality of outlet openings 510 between the fuel cells and the adjacent interconnects. Side surfaces 511 and 513 may be closed side surfaces, meaning that the fuel cells are sealed to the adjacent interconnects along the side surfaces 511, 513 (i.e., there are no inlet or outlet openings on side surfaces 511 and 513). The stack 501 may be assembled by alternately stacking SOFCs 1 with interconnects 9 (such as interconnect 9 shown in FIGS. 3A and 3B) so that the anode facing surfaces of the interconnects 9 (see FIG. 3B) face the anode-sides of the fuel cells and the cathode facing surfaces of the interconnects 9 (see FIG. 3A) face the cathode sides of the fuel cells. The first sides 301 of the interconnects 9 may be located along open side surface 507 of the stack, the second sides 302 of the interconnects 9 may be located along open side surface 509 of the stack, and the third and fourth sides 303, 304 of the interconnects 9 may be located along the closed side surfaces 511 and 513 of the stack.

The stack 501 also includes riser channels 16a, 16b that extend through the fuel cells and interconnects of the stack 501 (shown in dashed lines in FIG. 5A). In operation, a first reactant 515 (e.g., fuel) may flow into the stack 501 through the inlet riser channel 16a, portions of the first reactant may flow into spaces between the anode sides of the fuel cells and the adjacent interconnects of the stack, and then out of the stack 501 via the outlet riser channel 16b. A second reactant 517 (e.g., air) may flow into the stack 501 through the inlet openings on the side surface 507 of the stack 501 into the spaces between the cathode sides of the fuel cells and the adjacent interconnects of the stack and then out of the stack 501 via the outlet openings 510. The stack 501 may include seals, such as seals 15a, 15b, 15c and 15d shown in FIGS. 3A and 3B, which prevent the reactants from mixing within the stack 501 and the fuel from leaking out of the sides 507, 509, 511, 513 of the stack 501.

FIG. 5A schematically illustrates a first embodiment method of testing the fuel cell stack 501 for defects, such as electrolyte cracks or defective seals. As shown in FIG. 5A, a fluid 515 (e.g., a gas) comprising ammonia is provided in the first reactant flow path (i.e., the fuel flow path) of the stack. The ammonia may comprise gaseous ammonia from an ammonia source 519 that may be optionally mixed with one or more other gases and flowed through the fuel flow path (i.e., through the inlet riser channel 16a, into the spaces between the anode sides of the fuel cells and the adjacent interconnects and out through the outlet riser channel 16b) in a first portion of the stack 501. A second fluid 517 (e.g., a gas, such as air) which preferably does not contain any ammonia is optionally provided in the second reactant flow path (e.g., the air flow path) of the stack 501. Alternatively, the second fluid 517 flow may be omitted.

An ammonia detector 521 is positioned within or adjacent to a second portion of the stack 501 that is separated from the first portion of the stack which contains the fuel reactant flow path (i.e., the second portion of the stack may be separated from the first portion containing the fuel reactant flow path by one or more electrolytes and/or seals). As shown in FIG. 5A, the ammonia detector 521 may be located adjacent to the open side surface 509 of the stack 501 containing the outlet openings 510 of the air flow path. The detector 521 may be configured to detect for the presence of ammonia in the second fluid 517 as it exits the outlet openings 510 of the stack and/or ammonia leaking out of the openings 510 when no second fluid is used. A detected quantity of ammonia in the second fluid 517 and/or leaking from openings 510 may indicate the existence of a defect in the stack 501, such as a small crack in the electrolyte or a defective seal that allows a portion of the ammonia-containing first fluid 515 in the fuel flow path in the first portion of the stack to leak into the air flow path and out of the stack through an air outlet opening 510. The ammonia detector 521 may be located over or may be moved to various positions adjacent to the open side surface 509 of the stack.

In some embodiments, multiple ammonia detectors 521 may be placed at different positions adjacent to the side surface 509 of the stack. A location and/or type of defect may be identified based on the location(s) at which ammonia is detected in the second fluid 517 or leaking from openings 510, and optionally the quantity of ammonia detected at each location.

The ammonia detector 521 may also be located at or may be moved to various positions adjacent to the open surface 507 and/or the closed side surfaces 513, 515 of the stack. The detection of ammonia adjacent to the closed side surfaces 513, 515 may indicate that one or more seals (e.g., the strip seals 15c or window seals 15d shown in FIGS. 3A and 3B respectively) that seal the fuel cells to the adjacent interconnects along the closed side surfaces 513, 515 of the stack 501 are defective. Alternatively, as described with respect to FIGS. 6A and 6B, the detector 521 may be a large sheet of colorimetric paper which covers the entire side surface of the stack and may cover all or portions of plural side surfaces of the stack to detect detects on plural side surfaces at the same time. Thus, there is no need to move such a detector 521.

Based on the detection of ammonia by the ammonia detector 521, one or more defective components of the fuel cell stack 501, such as a cracked electrolyte or defective seal, may be identified and located. The defective component(s) of the stack may be removed and replaced prior to operation of the stack.

The ammonia detection method may be performed at a temperature that is less than an operating temperature of the fuel cell stack 501 (i.e., less than 750° C., such as less than 100° C.). For example, the method may be performed at a temperature between about 0° C. and about 50° C., such as between about 20° C. and about 30° C.

The ammonia detector 521 may comprise any detector that can detect the presence or quantity of gaseous ammonia. Various suitable detectors for gaseous ammonia are known in the art, including without limitation detectors using metal oxide-based sensing elements, catalytic metal or polymer-based ammonia sensors, as well as spectroscopic and photoionization ammonia detectors. In various embodiments, the ammonia detector 521 may comprise a colorimetric sensor in which the sensing element (e.g., a test paper or gas tube) includes a chemical reagent that is sensitive to ammonia and causes a perceptible change in color of the sensing element when exposed to ammonia.

FIG. 5B illustrates an alternative embodiment in which ammonia from an ammonia source 519 is provided in the portion of the fuel cell stack 501 containing the air flow path and the ammonia detector 521 is provided within or adjacent to the fuel flow path of the fuel cell stack 501. In this embodiment, the ammonia-containing fluid 515 flows through the inlets openings on the open side surface 507 of the stack 501, into the spaces between the cathode sides of the fuel cells and the adjacent interconnects and out through the outlet openings 510 on the opposite open side surface 509 of the stack 501. The ammonia detector 521 may be positioned within or adjacent to a fuel riser channel 16a, 16b. For example, the ammonia detector 521 is FIG. 5B is located inside of the fuel outlet riser channel 16b. A detected quantity of ammonia in the riser channel 16b may indicate the existence of a defect in the stack 501, such as a small crack in the electrolyte or a defective seal that allows a portion of the ammonia-containing fluid 515 in the air flow path to leak to the riser channel 16b in the fuel flow path of the stack 501. The ammonia detector 521 may extend over all or a portion of the riser channel 16b, or may be moved to various positions within the riser channel 16b. A location and/or type of stack defect may be identified based on the location(s) and/or quantity of detected ammonia in the riser channel 16b.

Figure 6A:
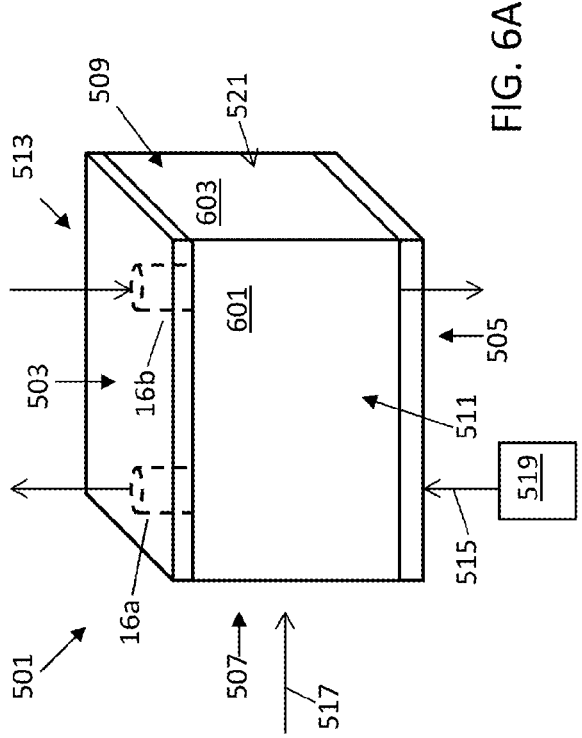
FIGS. 6A and 6B are respective perspective and front views which schematically illustrate a fuel cell stack testing method using an ammonia detector comprising planar surfaces that are positioned adjacent to side surfaces of the fuel cell stack.
Figure 6B:
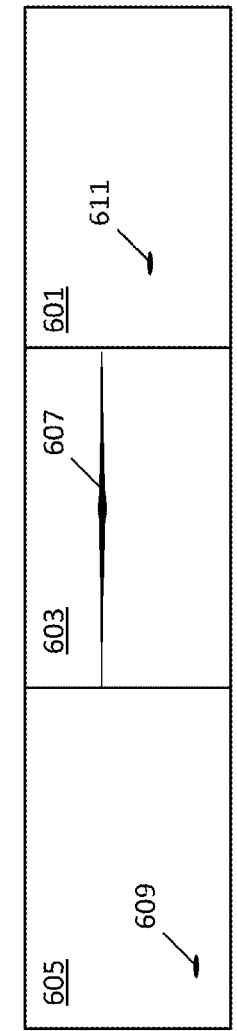

FIGS. 6A-6B illustrate an exemplary embodiment of an ammonia detection technique for detecting fuel cell stack defects. In this embodiment, the ammonia detector 521 comprises one or more planar surfaces 601, 603, 605 that extend over one or more side surfaces 509, 511, 513 of the fuel cell stack 501. The ammonia detector 521 may include planar surfaces that extend over all four side surfaces 507, 509, 511, 513 of the stack if no air 517 flows through the inlet openings on open side surface 507. Preferably, the planar surface(s) 601, 603, 605 of the ammonia detector 521 extend over at least about 50%, such as 50-100% (e.g., 50-90%, including 60-75%) of the surface area of the respective side surface(s) of the fuel cell stack 501. As shown in FIG. 6A, the planar surface 603 adjacent to the open side surface 509 of the stack 501 extends adjacent to all of the air outlet openings 510 of the stack 501. Planar surfaces 601 and 605 are adjacent to the closed side surfaces 511, 513 of the stack 501 and extend adjacent to all of the seals on the closed side surfaces 511, 513. The ammonia detector 521 may comprise a unitary structure that is wrapped around multiple side surfaces of the stack 501. Alternatively, the planar surfaces 601, 603, 605 may comprise separate structures, and each planar surface 601, 603, 605 can be made up of multiple smaller structures.

The detector 521 of FIGS. 6A-6B may comprise a flexible sheet or membrane (e.g., a paper or cloth) that is impregnated with an ammonia-sensitive chemical reagent that induces a localized change in color when exposed to gaseous ammonia. The sheet may be placed over one or more side surfaces of the stack 501 (e.g., side surfaces 509, 511 and 513 in FIG. 6A) while ammonia-containing gas is flowed through the fuel flow path (i.e., through the inlet riser channel 16a, into the spaces between the anode sides of the fuel cells and the adjacent interconnects and out through the outlet riser channel 16b) in a first portion of the stack 501. A second fluid 517 (e.g., a gas, such as air) which does not contain ammonia may optionally be flowed through the air flow path of the stack 501.

The detector 521 may then be removed from the stack 501, and the planar surfaces 601, 603, 605 that were located adjacent to the side surfaces of the stack 501 may be inspected (e.g., visually or using an optical sensing device) to detect any change in coloration. For example, planar surface 603 that was adjacent to the open side surface 509 of the stack 501 includes a region of discoloration 607 that corresponds to the location of an air outlet opening 510 of the stack. This change in coloration of the detector 521 may indicate a defect (e.g., an electrolyte crack and/or a defective riser seal 15a, 15b) in the fuel cell adjacent to the air outlet opening 510. Planar surfaces 601, 605 include regions of discoloration 609, 611 that may be indicative of defective seals along the closed side surfaces 511, 513 of the stack.

Any other gas besides ammonia which can be readily detected (e.g., colorimetrically detected) may be used instead, such as gases other than air and fuel (e.g., hydrogen, methane, natural gas, pentane, propane and other hydrocarbon fuels) which are used during normal stack operation to generate electricity.

Figure 7:
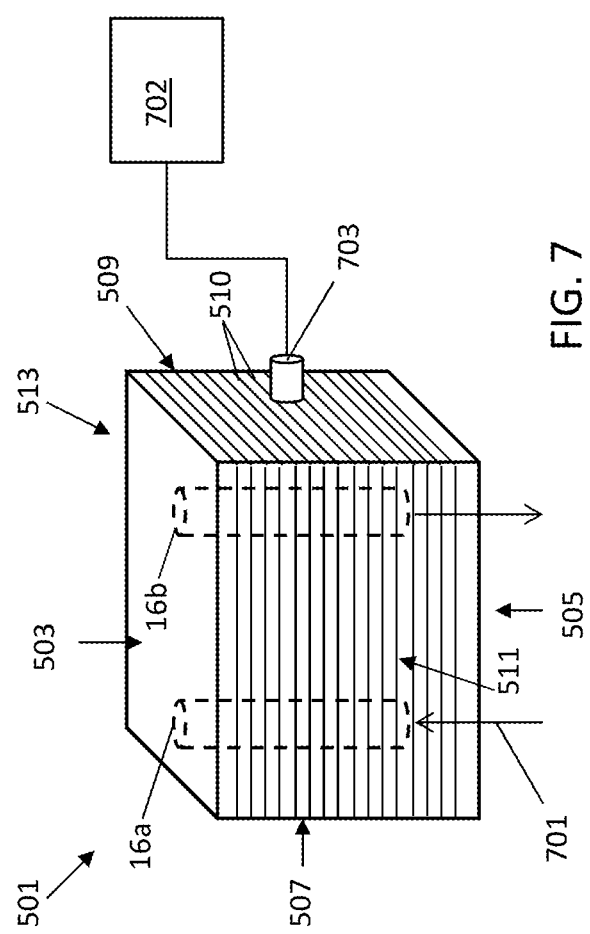
FIG. 7 schematically illustrates a perspective view of a fuel cell stack testing method using a microphone to detect audio signals indicative of a stack defect according to an embodiment.

FIG. 7 illustrates another embodiment method for accurate, rapid and non-destructive testing of fuel cell stacks that can be performed at a temperature significantly below the operating temperature of the stack, including at ambient temperature. In this embodiment, a pressurized fluid 701 is provided in a first reactant (e.g., fuel) flow path of the stack 501, an audio signal is detected using a microphone 703 positioned within or adjacent to a second portion of the stack that is separated from the fuel flow path (e.g., by one or more electrolyte(s) and/or seal(s)), and the presence of a defect in the stack 501 is determined based on the detected audio signal.

In this embodiment, a fluid 701 (e.g., a gas, which may be fuel, air or any suitable gas or gas mixture, such as nitrogen or noble gas) is flowed (e.g., under suitable pressure) in the fuel flow path of the fuel cell stack 501. The stack 501 may be substantially identical to the stack described above with reference to FIG. 5A. The microphone 703 is positioned within or adjacent to a second portion of the stack 501 that is separated from the first portion of the stack which contains the fuel reactant flow path (i.e., the second portion of the stack may be separated from the first portion containing the fuel reactant flow path by one or more electrolytes and/or seals). As shown in FIG. 7, the microphone 703 may be located adjacent to the open side surface 509 of the stack 501 containing the outlet openings 510 of the air flow path, and may detect an audio signal from the stack 501. The detected audio signal may be converted to an electronic representation of the audio signal which may be provided to a logic device 702 (e.g., a computer) connected to the microphone 703 (e.g., via a wired or wireless link). The logic device 702 may have a memory and a processor coupled to the memory, wherein the processor may be configured with processor-executable instructions to perform various functions, including analyzing the detected audio signal from the microphone, and determining whether the stack contains a defect based on the analysis of the detected audio signal.

In embodiments, the fuel flow path of the fuel cell stack 501 (e.g., risers 16a, 16b) may be filled with the fluid 701 under pressure, and the outlets of the riser channels 16a, 16b of the stack 501 may be closed (e.g., capped) to enclose the pressurized fluid 701 within the stack 501. The fuel cell stack 501 may produce a localized characteristic sound (e.g., an audible sound, such as a sound having frequencies in a range between 20 and 20,000 Hz) that is indicative of a stack defect and the microphone 703 may detect this characteristic sound. For example, as a portion of the fluid 701 leaks from the fuel flow path into the air flow path due to a crack in the electrolyte or a defective seal, the fluid 701 may produce a low intensity "hissing" sound. This characteristic sound may be picked up by a microphone 703 positioned proximate to the defect.

The logic device 702 may analyze the detected audio signal from the microphone 703 to determine whether the detected audio signal indicates the presence of a defect in the stack 501. For example, the logic device may be configured to analyze one or more characteristics of the detected audio signal (e.g., a frequency and/or amplitude characteristic of the signal) to determine whether the characteristic is indicative of the presence of a stack defect. In one embodiment, the logic device 702 may compare a value of the characteristic of the detected audio signal to a baseline or threshold value (e.g., stored in a lookup table) to determine whether the value is indicative of a stack defect. The baseline or threshold value may be derived from audio signal(s) detected from stacks which are known to contain or to not contain defects. In other embodiments, the logic device 702 may compare the one or more characteristics of the detected audio signal to a statistical distribution of the characteristics from a plurality detected audio signals measured at a plurality of locations over the stack 501 and/or from a plurality of different stacks, and determine whether a given detected audio signal indicates the presence of a defect based on the comparison to the statistical distribution.

The microphone 703 may be located over or may be moved to various positions adjacent to the open side surface(s) 509 and/or 507 of the stack. For example, the microphone 703 may positioned within or adjacent to each of the air outlet openings 510 on the open side surface 509 of the stack 501 and detect an audio signal from each of the outlet openings 510. In embodiments, multiple microphones 703 (e.g., an array of microphones 703) may be utilized.

In an alternative embodiment, the pressurized fluid 701 may be provided in the air flow path of the fuel cell stack 501, and the microphone 703 may be positioned within or adjacent to a fuel riser channel 16a, 16b of the stack 501.

The microphone 703 may also be located at or may be moved to various positions adjacent to the closed side surfaces 513, 515 of the stack. The audio signals detected from the closed side surfaces 513, 515 may be analyzed to determine whether there are any defects in the seals that seal the fuel cells to the adjacent interconnects along the closed side surfaces 513, 515 of the stack 501 (e.g., the strip seals 15c or window seals 15d shown in FIGS. 3A and 3B respectively).

When a defect is determined based on an analysis of the detected audio signal, one or more defective components of the fuel cell stack 501, such as a cracked electrolyte or defective seal, may be identified and located. The defective component(s) of the stack may be removed and replaced prior to operation of the stack.

The method of FIG. 7 may be performed at a temperature that is less than an operating temperature of the fuel cell stack 501 (i.e., less than 750° C., such as less than 100° C.). For example, the method may be performed at a temperature between about 0° C. and about 50° C., such as between about 20° C. and about 30° C.

While solid oxide fuel cell stacks, electrolytes and interconnects were described above in various embodiments, embodiments can include any other fuel cell systems, such as molten carbonate or PEM fuel cell systems or stacks.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

Further, any step or component of any embodiment described herein can be used in any other embodiment.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method of testing fuel cell stack components assembled in a fuel cell stack, comprising:
   providing a fluid in a first reactant flow path in a first portion of the fuel cell stack;
   detecting the presence of the fluid using a detector positioned within or adjacent to a second portion of the fuel cell stack that is separated from the first portion of the fuel cell stack; and
   determining the presence or absence of a defect in the stack based on detecting the presence of the fluid.

2. The method of claim 1, wherein the fluid comprises ammonia and the detector comprises an ammonia detector.

3. The method of claim 1, wherein at least one of:
   (a) the second portion of the fuel cell stack is separated from the first portion of the fuel cell stack by at least one of a fuel cell electrolyte and a seal; and
   (b) the detector is positioned within or adjacent to a second reactant flow path of the fuel cell stack.

4. The method of claim 1, wherein the detector is positioned within or adjacent to a second reactant flow path of the fuel cell stack and the fuel cell stack is externally manifolded for the second reactant and comprises inlet and outlet openings of the second reactant flow path on one or more open side surfaces of the stack, and the detector is positioned adjacent to at least one outlet opening on an open side surface of the stack, and the fuel cell stack is internally manifolded for the first reactant and the fluid is provided into a first reactant riser opening.

5. The method of claim 4, wherein the detector comprises a planar surface that extends adjacent to multiple outlet openings on the open side surface of the stack.

6. The method of claim 5, wherein at least one of:
   (a) the planar surface of the detector extends adjacent to all of the outlet openings on the open side surface of the stack; and
   (b) the detector comprises a sheet having a planar surface that contains a material that is sensitive to a constituent of the fluid such that exposure to the constituent causes a localized change in coloration of the sheet;
   (c) the planar surface extends over at least about 50% of the surface area of the open side surface of the stack; and
   (d) the detector comprises a flexible sheet that extends over the open side surface and at least one additional side surface of the fuel cell stack.

7. The method of claim 5, wherein the detector comprises a sheet having a planar surface that contains a material that is sensitive to a constituent of the fluid such that exposure to the constituent causes a localized change in coloration of the sheet, and wherein at least one of:
   (a) the constituent of the fluid comprises ammonia; and
   (b) the method further comprises determining a location of a defect in the stack based on a location of the detected fluid based on a local change in coloration of the sheet.

8. The method of claim 1, wherein the first reactant flow path is a fuel path through at least one riser channel that extends through the fuel cell stack through a plurality of fuel cells separated by a plurality of interconnects, and the fuel cell stack comprises a second externally-manifolded air flow path, and the detector is positioned within or adjacent to the air flow path.

9. The method of claim 1, wherein the first reactant flow path is an externally manifolded air flow path, and the fuel cell stack comprises a second fuel flow path through at least one riser channel that extends through the fuel cell stack through a plurality of fuel cells separated by a plurality of interconnects, and the detector is positioned within or adjacent to the at least one riser channel.

10. The method of claim 1, wherein the stack comprises a plurality of fuel cells separated by a plurality of interconnects and a plurality of seals that seal the plurality of fuel cells to the plurality of interconnects along at least one closed side surface of the fuel cell stack, and the detector is positioned adjacent to the at least one closed side surface of the stack.

11. The method of claim 10, wherein at least one of:
    (a) the detector comprises a planar surface that is positioned adjacent to all of the seals along the at least one closed side surface of the stack; and
    (b) the detector comprises a flexible sheet having a planar surface that contains a material that is sensitive to a constituent of the fluid such that exposure to the constituent causes a localized change in coloration of the sheet, and the flexible sheet is positioned adjacent to at least two side surfaces of the stack.

12. The method of claim 10, wherein the detector comprises a flexible sheet having a planar surface that contains a material that is sensitive to a constituent of the fluid such that exposure to the constituent causes a localized change in coloration of the sheet, and the flexible sheet is positioned adjacent to at least two side surfaces of the stack, and wherein at least one of:
    (a) the constituent of the fluid comprises ammonia; and
    (b) the flexible sheet is positioned adjacent to at least one closed side surface and at least one open side surface of the stack, wherein the at least one open side surface comprises at least one outlet opening of a second reactant flow path.

13. The method of claim 1, wherein:
    (a) the defect in the stack comprises at least one of a defective seal and a crack in an electrolyte of the fuel cell stack;
    (b) the method is performed at a temperature between about 0° C. and about 50° C.; and
    (c) the fuel cell stack comprises a solid oxide fuel cell stack.

14. The method of claim 1, wherein the defect in the stack comprises at least one of a defective seal and a crack in an electrolyte of the fuel cell stack, the method further comprising:
    replacing the at least one of the defective seal and the cracked electrolyte in response to determining the presence of a defect in the stack.

15. A method of testing fuel cell stack components assembled in a fuel cell stack, comprising:
    providing a pressurized fluid in a first reactant flow path of the fuel cell stack;
    detecting an audio signal using a microphone positioned within or adjacent to a second portion of the stack that is separated from the first reactant flow path; and
    determining the presence or absence of a defect in the stack based on the detected audio signal.

16. The method of claim 15, wherein at least one of:
    (a) the second portion of the fuel cell stack is separated from the first reactant flow path by at least one of a fuel cell electrolyte and a seal;
    (b) the method is performed at a temperature between about 0° C. and about 50° C.;
    (c) the fuel cell stack comprises a solid oxide fuel cell stack; and
    (d) providing the pressurized fluid comprises flowing the fluid into the first reactant flow path of the fuel cell stack and sealing outlet to the first reactant flow path to contain the fluid within the first reactant flow path at elevated pressure.

17. The method of claim 15, wherein determining the presence of a defect comprises analyzing the detected audio signal using a logic device coupled to the microphone to determine a characteristic of the detected audio signal, and determining the presence of a defect when the characteristic is indicative of a defect.

18. The method of claim 15, wherein the stack is externally manifolded for a second reactant and comprises inlet and outlet openings of a second reactant flow path on one or more open side surfaces of the fuel cell stack, and the microphone is positioned adjacent to at least one outlet opening on an open side surface of the fuel cell stack.

19. The method of claim 18, wherein an audio signal is detected from within or adjacent to each outlet opening on the open side surface of the fuel cell stack.

20. The method of claim 15, wherein at least one of:
(a) the first reactant flow path is a fuel path through at least one riser channel that extends through the fuel cell stack through a plurality of fuel cells separated by a plurality of interconnects, and the fuel cell stack comprises a second externally-manifolded air flow path, and the microphone is positioned within or adjacent to the air flow path;
(b) the first reactant flow path is an externally manifolded air flow path, and the fuel cell stack comprises a second fuel flow path through at least one riser channel that extends through the fuel cell stack through a plurality of fuel cells separated by a plurality of interconnects, and the microphone is positioned within or adjacent to the at least one riser channel; and
(c) the fuel cell stack comprises a plurality of fuel cells separated by a plurality of interconnects and a plurality of seals that seal the plurality of fuel cells to the plurality of interconnects along at least one closed side surface of the fuel cell stack, and the audio signal is detected using a microphone positioned adjacent to at least one seal along a closed side surface of the fuel cell stack.

* * * * *